United States Patent [19]

Morlock et al.

[11] 4,088,597
[45] May 9, 1978

[54] IODOPHOR SOLUTION

[75] Inventors: Gerhard Morlock; Gerhard Stehlik, both of Hanau, Germany

[73] Assignee: Deutsche Gold- und Silber-Scheideanstalt vormals Roessler, Frankfurt, Germany

[21] Appl. No.: 805,872

[22] Filed: Jun. 13, 1977

[51] Int. Cl.² .................. A61K 33/18; A61L 13/00; C11D 3/48
[52] U.S. Cl. .................. 252/106; 252/89 R; 252/136; 252/173; 252/531; 252/538; 252/539; 252/DIG. 28; 252/DIG. 14; 424/150
[58] Field of Search ............. 252/106, 89, 136, 531, 252/538, 539, 173, DIG. 2, DIG. 14; 424/150

[56] References Cited

U.S. PATENT DOCUMENTS

| | | | |
|---|---|---|---|
| 2,706,701 | 4/1955 | Beller | 252/106 X |
| 2,758,049 | 8/1956 | Dienna | 424/81 |
| 2,977,315 | 3/1961 | Scheib | 252/106 |
| 3,150,096 | 9/1964 | Schmidt | 252/106 |
| 3,525,696 | 8/1970 | Schmidt | 252/106 |
| 3,650,966 | 3/1972 | Bakka | 252/106 |
| 3,793,222 | 2/1974 | Haschke | 252/180 |
| 3,950,261 | 4/1976 | Landi | 424/150 |
| 3,984,341 | 10/1976 | Haschke | 252/106 |

FOREIGN PATENT DOCUMENTS

| | | | |
|---|---|---|---|
| 843,183 | 1/1977 | Belgium | 252/106 |
| 1,171,112 | 5/1964 | Germany | 252/106 |
| 2,527,795 | 12/1976 | Germany | 252/106 |
| 7,605,297 | 12/1976 | Netherlands | 252/106 |

Primary Examiner—Dennis L. Albrecht
Attorney, Agent, or Firm—Cushman, Darby & Cushman

[57] ABSTRACT

There is prepared an iodophor solution comprising
(a) 0.5 to 3 weight percent iodine,
(b) 10 to 30 weight percent phosphoric acid,
(c) 5 to 30 weight percent acetic acid, and
(d) 0.5 to 20 weight percent of a polymer having an average molecular weight between 500 and 10,000 and consisting essentially of repeating units of the general formula

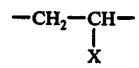

where X in 90 to 65% of the cases is COOH, in 10 to 35% of the cases is

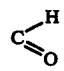

and in 0 to 10% of the cases is CH₂OH and/or CN and/or

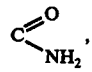

the side chains being distributed statistically at random. The solution is made up with water to 100 weight percent. Preferably there is present hydrogen iodide, alkali metal iodide, alkaline earth metal iodide or ammonium iodide. Also there can be present a wetting agent such as sodium lauryl sulfate or sodium dodecylbenzene sulfonate or sodium dihexylsulfosuccinate.

19 Claims, No Drawings

IODOPHOR SOLUTION

BACKGROUND OF THE INVENTION

The invention is directed to an iodophor solution comprising a mixture of water, 0.5 to 3 weight percent of iodine, 10 to 30 weight percent phosphoric acid, an organic acid and a polymer. The percentages are based on the total weight of the mixture.

Iodophor solutions are aqueous solutions of complex iodine compounds with a content of active iodine of about 0.5 to about 3 weight percent which after dilution with water to the particular active iodine concentration for the use intended are used as disinfectants.

Iodophor solutions based on different formulations are known. They are preferably produced from concentrates having a high active iodine content of about 15 to about 30 weight percent by mixing in a material which dilutes the composition.

Thus, there are known iodophors and iodophor solutions based on polyvinyl pyrrolidone (Beller U.S. Pat. No. 2,706,701). These types of iodophors and iodophor solutions, however, have the disadvantage that only a maximum of 67 percent of their total iodine content is available as active iodine for disinfection purposes, to be sure, according to the work of Robert F. Cournoyer, Polymer Chemistry Edition 12, 603-612 (1964), even then if there is employed to produce the polyvinyl pyrrolidone-iodophors only elementary iodine and there are not used iodine compounds.

There are also known iodophors on a pure tenside basis, Scheib U.S. Pat. No. 2,977,315. In these iodophors the ratio of active iodine to total iodine generally is somewhat more favorable than with polyvinyl pyrrolidone iodophors. However, they have the disadvantage that they have extremely high viscosity and therefore can no longer be pumped. Therefore there must be added to them before their use in industrial systems up to 65% of a relatively expensive, viscosity lowering agent, e.g., hydroxyacetic acid (according to Cantor, German Pat. No. 1,171,112), in order to make the products pumpable again and therewith generally for the first time available industrially.

Besides, these iodophors based on tensides because of their strong tendency to foam are completely unsuited for many industrial processes, for example, in the newer methods of jet purification, high pressure jet purification and spraying purification in breweries, where the development of a foam is undesired and hence, they cannot be used in such places.

Furthermore, there are known iodophor solutions which consist of phosphoric acid, citric acid, sodium polymethacrylate, sodium xylene sulfonate, iodine, hydriodic acid and water (Schmidt U.S. Pat. No. 3,150,096). In these iodophor solutions the relative portions of the various components are of critical significance, e.g., the amount of iodine added must be between 0.5 and 3.0 percent. Therefore, based on their formulation there cannot be produced high iodine containing iodophor concentrates. These iodophor solutions thus cannot be prepared by diluting correspondingly higher iodine containing concentrates but their production is tied each time to its own relatively expensive iodine solubilization process.

A further critical disadvantage of these known iodophor solutions is that for solubilization of iodine there must be added surface active compounds (sodium xylene sulfonate) so that there cannot be produced detergent free iodophor solutions.

It is also known to produce a non-foaming iodophor by mixing while heating to about 50°-120° C for about 0.75-15 hours (1) about 10-30 weight percent of elementry iodine and (2) about 90-70 weight percent of an aqueous solution consisting essentially of (a) about 7-30 weight percent of a polycarboxylic acid or polycarboxylate or mixtures thereof having at least 65 carboxyl or carboxylate groups per molecule, (b) about 0-20 weight percent of an alkali metal iodide, ammonium iodide or mixtures thereof or at least one lower monovalent aliphatic alcohol, (c) about 0-20 weight percent of a non-volatile multibasic mineral acid, a multibasic oxycarboxylic acid or mixtures of such acids which do not substantially reduce elementary iodine and (d) water in amount sufficient that the aqueous solution comprises 100 weight percent (Haschke U.S. Pat. No. 3,984,341). The entire disclosure of Haschke is hereby incorporated by reference and relied upon.

SUMMARY OF THE INVENTION

The object of the invention is an iodophor solution which is made up with water to 100 weight percent. The solution comprises:
 (a) 0.5 to 3 weight percent iodine,
 (b) 10 to 30 weight percent phosphoric acid,
 (c) an organic acid, and
 (d) a polymer.

Component (c) is 5 to 30 weight percent acetic acid and component (d) is 0.5 to 20 weight percent of a polymer having an average molecular weight between 500 and 10,000 and consisting essentially of repeating units of the general formula $$-CH_2-CH-\atop\ \ \ \ \ \ \ |\atop\ \ \ \ \ \ \ X$$

where X in 90 to 65% of the cases is COOH, in 10 to 35% of the cases is

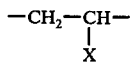

and in 0 to 10% of the cases is CH$_2$OH and/or CN and/or

the side chains being distributed statistically at random.

The iodophor solutions of the invention are homogeneous and what is especially advantageous for the practical use, have a high phosphoric acid content and are, easily movable and pumpable. Upon dilution to the concentration of use there either results no foaming or only very weak foaming of the disinfection solution of the invention.

The addition of disinfection agents generally serves to maintain or restore specific hygienic operating conditions in various regions of industry and agriculture, which can influence or damage the health of people either directly, e.g., the operating conditions in hospitals, or indirectly via the manufacture, e.g., the products of the food industry or agriculture.

The addition and the effectiveness of disinfection agents therefore are not only of interest in the factories but as a rule are also under public control through authorities, official public boards or scientific-industrial associations.

Therefore, specific properties of iodophor solutions have already been established by legal provisions, standards, norms or official determinations.

These rules describe different types of compositions for the iodophor solutions according to the place of addition and the intended use. For example, an iodophor solution for use as a wound disinfectant along the idea of the known tincture of iodine must have different properties than, e.g., an iodophor solution for high pressure jet purification of brewery pans.

A producer of iodophor solutions thus has an advantage if he can produce as many as possible of these different regulated types of iodophor solutions and if for their production he is able to add the least possible raw materials, particularly only a single iodophor concentrate as the source of iodine.

Therefore, a two step process with the production of the most universally addable iodophor as the raw material and iodine source in the first step and the packaging or finishing production of various, industrially interesting iodophor solutions in the second step is especially advantageous.

The mentioned control over the properties of iodophor solutions depending on the different regulations according to the purpose and place of addition, however, has a common characteristic, which is based on the pH dependence of the disproportionation reaction of the iodine in aqueous solution to iodide-hypoidide. This disproportionation and the loss of disinfecting activity of the iodine associated with it increases quicker at higher pH values of the aqueous iodine solution and begins at about pH=6. The mentioned regulations therefore all contain a specification that the pH of every iodophor disinfection solution must be in the acid pH range whereby the iodophor disinfection solution must be producible by each user (e.g., brewery, dairy farm, hospital) merely by a suitable dilution of the iodophor solution with water.

The phosphoric acid serving to stabilize the pH therefore must be contained already in sufficient amounts in the iodophor solutions which are sold to the respective users for the production of iodophor disinfection solutions.

The iodophor solutions of the invention can be produced in two basically different ways.

The first, generally industrially more advantageous way begins with the production of high iodine containing, easily movable and pumpable, homogeneous, storable and detergent free iodophor concentrates which are characterized by the iodine solubilization taking place with the copolymerizate to be used in the invention. The production of the true iodophor solutions with 0.5 to 3 weight percent active iodide from these iodophor concentrates therefore only requires an easily carried out dilution process in which only easily handleable materials are added.

The particular advantage of this two step process for the production of the iodophor solutions of the invention is that very many different packaged, i.e., specially prepared for very different purposes of use, iodophor solutions can be produced in a relatively short time by pure mixing or dilution processes without again requiring in addition the protracted iodine solubilization and the disagreeable contact with elementary iodine.

However, independent from this there is the direct production of the iodophor solutions of the invention directly from the constituents iodine, copolymerizate, water, acetic acid and phosphoric acid as the second basic way of production. In special cases this is also advantageous, e.g., for the production of relatively large amounts only of a quite specific type of iodophor solution.

The iodophor solubilization in every case takes place suitably in a closed, corrosion resistant, heatable and coolable stirred container at internal temperatures between about 40° and about 100° C, preferably between 60° and 80° C, and reaction times of 2 to 10 hours. The solution of the iodine can be accelerated by organic and/or inorganic iodine solvents wherein as organic iodine solvents there can be added monohydric alcohols with 1 to 4 carbon atoms, e.g., alkanols such as methyl alcohol, ethyl alcohol, propyl alcohol, isopropyl alcohol, butyl alcohol and sec. butyl alcohol with the propanols being preferred, and as inorganic solvents hydrogen iodide and/or the alkali metal iodides, e.g., sodium iodide, lithium iodide and potassium iodide and/or the alkaline earth metal iodides, e.g., magnesium iodide, calcium iodide and barium iodide and/or ammonium iodide.

The named alcohols can be added in such amounts that their portion in the finished iodophor solution amounts to 0.1 to 10 weight percent, the named inorganic iodine solvents in such amounts that their portion in the finished iodophor solution is 0.1 to 3 weight percent.

The named organic and/or inorganic solvents are of no basic significance, however, in the space of the present invention, i.e., they do not serve as true iodine solubilizers. However, because of their low molecular weight nature they can contribute to the acceleration ("iodine-carrier") of the iodine solubilization by the copolymerizate. For reasons of cost their addition, however, is only meaningful if a high space-time-yield must be produced because of limited capacity of the equipment.

The packaging or finishing dilution of the iodophor concentrate for production of the iodophor solutions of the invention is characterized by the addition of water, acetic acid and phosphoric acid to the iodophor concentrate which is suitably carried out in a heatable or coolable stirred container at temperatures between 10° and 60° C, preferably between 30° and 40° C. The manner of bringing together the various components of the mixture is not critical, merely to avoid complications the phosphoric acid should be added last and in portions.

The entire mixing process is normally completed in a maximum of one hour. Higher mixing temperatures between 30° and 60° C, however, accelerate it so quickly that it frequently has taken place in 5 to 10 minutes.

In the following the starting materials for the production of the iodophor solutions of the invention are again summarized and described:

As iodine there can be used both resublimed iodine and industrial crude iodine. The crude iodine, however, should not contain any insoluble constituents which otherwise in any case make necessary a filtration of the iodophor solution.

The phosphoric acid is preferably added as highly concentrated 65 to 85% industrial acid. However, it can also be added as dilute phosphoric acid, so long as it is not necessary to exceed the maximum amount of water in the formulation due to using the dilute phosphoric acid.

The acetic acid is preferably added as glacial acetic acid of industrial quality. The same conditions as to using dilute phosphoric acid also apply to using dilute aqueous acetic acid.

The polymers used in the iodophor solutions of the invention have an average molecular weight between 500 and 10,000, preferably between 1500 and 5400. Their repeating units are derived from 90 to 65% acrylic acid and 10 to 35% acrolein. Additionally, up to a total of 10% of the units can be derived from allyl alcohol and/or acrylonitrile and/or acrylamide. The different units are arranged statistically at random in the molecule.

Preferably there are used those polymers which are derived from only acrylic acid and acrolein units, thus pure acrolein-acrylic acid copolymers. These can be produced by oxidative copolymerization of acrolein and acrylic acid in aqueous hydrogen peroxide solution at temperatures between about 60° and 80° C. A particularly suitable process for their production is described in Haschke German Pat. No. 1,942,556 and related Haschke U.S. Pat. No. 3,793,222. The entire disclosure of Haschke U.S. Pat. No. 3,793,222 is hereby incorporated by reference and relied upon.

Polymers which additionally have the other mentioned units can be produced in the same manner but with the co-use of corresponding amounts of allyl alcohol and/or acrylonitrile and/or acrylamide.

The polymers used are water soluble and have acid equivalent weights between about 78 and about 105.

For packaging or for special finishing there can be added to the iodophor solutions of the invention suitable materials whose main purpose is merely to modify the physical properties of the iodophor solutions. In their preferred form the latter are low viscosity liquids, however, they can also be changed into viscous iodine containing pastes, dispersions or emulsions in which the iodophor solutions of the invention are contained only as one phase besides other phases.

The suitable materials in this sense can be mixed in both together with the diluting agents acetic acid and water as well as separately after the portionwise addition of phosphoric acid. Thereby, they can be soluble or insoluble in the iodophor solution. In any case, they must remain inert to the essential materials of the invention. This is particularly true for their behavior against the solubilized iodine and the phosphoric acid. Other materials regulating the physical properties of the iodophor solutions are anion active detergents, e.g., the alkali and/or the ammonium salts and/or the free acids of sulfuric acid esters of fatty alcohols, e.g., sodium lauryl sulfate, sulfofatty acids, preferably sulfosuccinic acid esters, e.g., sodium dihexyl sulfosuccinate and sodium dioctyl sulfosuccinate, aromatic hydrocarbon sulfonic acids, e.g., sodium xylene sulfonate, araliphatic hydrocarbon sulfonic acids, e.g., sodium dodecyl benzene sulfonate, phosphoric acid esters, e.g., trioctyl phosphate, phosphonocarboxylic acids, e.g., methane diphosphonic acid, hydroxymethane diphosphonic acid or phosphono hydrocarbons. These kinds of wetting agents can be used in such amount that their portion in the finished iodophor solution amounts to 0.5 to 5 weight percent.

From these wetting agent containing iodophor solutions there are formed by suitable dilution with water iodophor disinfection solutions with higher wetting ability and with greatly reduced surface tension whereby the surface tension depending on the type and amount of wetting agent can be between 30 and 45 dyne/cm (measured according to ASTM D 971-50 ring method of Lecompte de Nouy).

Additionally, there can be worked into the iodophor solutions of the invention insoluble polishing agents such as sand, kaolin, china clay or pumice to form pasty products.

Additional substances modifying the physical properties of the iodophor solutions are thickening agents or so-called viscosity regulators such as pyrogenic or precipitated silica or hydrophilic swellable resinous polymers. The iodophor solutions produced in this way are especially suited as disinfection agents for deep disinfection of strongly sloping porous surfaces.

Besides the iodophor solutions of the invention for the widest range of dermatological purposes can be worked into emulsions which contain known skin care or skin protective agents such as lanolin or its derivatives, lecithin, cholesterol, unsaturated fatty oils, hydrogenated oils, cocoa butter or similar known agents.

The representative iodophor solutions in the following examples or the secondary products produced therefrom were tested according to the following methods:

Homogeneity Test

The homogeneity of the iodophor solutions was determined according to the stability test described in Australian Standard 1398-1972.

The iodophor solutions were designated as homogeneous if the active iodide content determined both by potentiometric titration with sodium thiosulfate of both a sample from the bottom of the container and a sample near the upper surface of the solution agree within the limits of titration error.

Viscosity Measurement

The stated viscosities were measured with a rotation viscosimeter (Haake VT-01 or VT-02) at 20° C.

Test of the Foaming Behavior

A definite advantage of the homogeneous, high phosphoric acid content iodophor solutions of the invention is that there are also producible therewith completely non-foaming disinfectant solutions. The careful and relevant test for use purposes of the foaming behavior of these disinfectant solutions therefore has a special significance for the evaluation of the present invention.

The foaming behavior of the disinfectant solutions adjusted to 20 ppm active iodine using dilution water with 15° dH (degree of German hardness) was tested in a "dynamic test" which is briefly described as follows. (1° dH corresponds to 17.85 ppm (CaCO$_3$).)

A high form 500 ml gas washing flask, outer diameter 5 cm is filled up to 40 mm with test liquid (disinfectant solution). Then there is blown in a dust and oil free compressed air stream at a rate of 2.0 ($\pm$0.04) l/min over a gas inlet tube with a frit located shortly above the bottom of the flask until the height of the foam peak formed first reaches a maximum. The height of this first foam peak maximum from the liquid surface measured in millimeters forms the basis for the following pattern of evaluation for the ability to foam.

| Pattern of Reporting for Evaluation of the Ability to Foam | |
|---|---|
| First Foam Height Maximum in Millimeters | Evaluation of the Foam Behavior of the Sample |
| Below 5 | not foaming |
| 5 to 30 | very weak foaming |
| 30 to 50 | weak foaming |
| 50 to 150 | Moderate foaming |
| over 150 | normal foaming |

The formation of foam in this "dynamic test" is a cyclic process in which there are alternate cycles of foam formation and cycles of breaking of the foam. The breaking of the foam then always predominates if the foam at a place of forming the foam peak is no longer sufficiently stable to carry the weight load of the foam peak lying thereover at this place.

The observation and evaluation of very many such "dynamic tests" for establishing the ability to foam, however, has shown that the wetting of the vessel wall in the rising of the first foam peak after the beginning of the test reduces the foam stability, so that in further progress of the "dynamic tests" the height of the foam peak as a rule no longer reaches the first foam peak maximum.

Other known test methods, e.g., the determination of the foam behavior according to DIN 53902 (German Industrial Standard 53902) or the Standard Method of Test for Foaming Properties of Surface Active Agents according to ASTM D 1173-53 (Ross-Miles Test) are completely unsuited as a basis for evaluation of the present invention since with them even with test solutions which already foam moderately in the "dynamic test" no measurable foam volumes form.

Now there follows a description of the production of iodophor concentrates which are used in the subsequent examples for the production of the iodophor solutions of the invention. In all cases the parts are parts by weight.

Iodophor A

In a closed heatable and coolable stirred container having an ascending condenser and suitable entering or feeding devices there were combined 30 parts crude iodine (98 weight percent)
20 parts potassium iodide and
50 parts of a 30 weight percent aqueous solution of an acrolein-acrylic acid copolymer having an average molecular weight of 4250 and an acid equivalent weight of 90 produced by oxidative copolymerization of 56 parts by weight of acrylic acid and 44 parts by weight of acrolein and the mixture was stirred for 3 to 4 hours at an internal temperature of 60° C. The total reaction mass was subsequently filtered over a porcelain frit (pore size G4). Thereby a residue remained on the porcelain frit only in exceptional cases.

The filtrate (100 parts) is a deep dark red-brown colored, homogeneous middle viscosity liquid having an active iodine content of about 30 weight percent.

Iodophor B

In the same type of container used to make Iodophor A there were combined 15 parts of crude iodine (98 weight percent)
15 parts isopropanol
70 parts of a 43 weight percent aqueous solution of an acrolein-acrylic acid copolymer having an average molecular weight of 1500 and an acid equivalent weight of 102 produced by oxidative copolymerization of 24 parts by weight of acrylic acid and 76 parts by weight of acrolein and the mixture stirred for 3 to 4 hours at 70° C internal temperature. The total reaction mass was subsequently filtered over a porcelain frit (pore size G4). Thereby a residue remained on the porcelain frit only in exceptional cases.

The filtrate formed (100 parts) is a deep dark red-brown colored, homogeneous, middle viscosity liquid with an active iodine content of about 15 weight percent.

Iodophor C

In the same type of container used to make Iodophor A there were combined 20 parts crude iodine (98 weight percent)
20 parts sodium iodide
5 parts phosphoric acid (85 weight percent)
5 parts isopropanol
50 parts of a 30 weight percent aqueous solution of an acrolein-acrylic acid copolymer having an average molecular weight of 8500 and an acid equivalent weight of 80 produced by oxidative copolymerization of 66 parts by weight of acrylic acid and 34 parts by weight of acrolein and the mixture stirred for 3 to 4 hours at 55° C internal temperature. The total reaction mass was subsequently filtered over a porcelain frit (pore size G4). Thereby a residue remained on the porcelain frit only in exceptional cases.

The filtrate formed (100 parts) is a deep dark red-brown colored, homogeneous, middle viscosity liquid with an active iodine content of about 20 weight percent.

The subsequently described iodophor solutions or preparations were produced with iodophors A, B and C. In all cases the parts stated again are parts by weight.

The compositions of the invention can comprise, consist essentially of or consist of the stated materials.

DESCRIPTION OF THE PREFERRED EMBODIMENTS

EXAMPLE 1

There were introduced into an open container equipped with a mechanical stirrer at room temperature while keeping the following sequence in succession 65 parts of water
10 parts of glacial acetic acid
10 parts of Iodophor A and in portions
15 parts of 85% phosphoric acid and the mixture stirred about 30 minutes.

The iodophor solution formed thereby is a homogeneous, deep red-brown, easily flowable liquid with an active iodine content of 3 weight percent which as such and also when diluted to a disinfectant solution containing 25 ppm of active iodine did not form any foam and is particularly suited for disinfection in high pressure spraying apparatus with the use of average hardness dilution water up to about 20° dH.

EXAMPLE 2

There were introduced into a closed stirred container adapted to be heated and cooled at 35° C internal temperature while keeping the following sequence in succession 20 parts of glacial acetic acid 2 parts of sodium lauryl sulfate as a 96% powder
51.3 parts of water
6.7 parts of Iodophor A and in portions
20 parts of 85% phosphoric acid
and the mixture stirred for about 5 minutes.

The iodophor solution formed thereby is a homogeneous, deep red-brown, easily flowable liquid with an active iodine content of about 2 weight percent which when diluted to a disinfectant solution containing 15 ppm of active iodine only foamed very weakly, had a surface tension of 42 dyne/cm and is particularly suited as a disinfectant solution for disinfection of pipe systems in circulating processes.

EXAMPLE 3

There were introduced into an open container equipped with a mechanical stirrer at room temperature while keeping the following sequence in succession
10 parts of glacial acetic acid
10 parts of sodium dihexyl sulfosuccinate 50% (balance water and isopropanol)
61.7 parts of water
3.3 parts of Iodophor B and in portions
15 parts of 85% phosphoric acid
and the mixture stirred about 30 minutes.

The iodophor solution formed thereby is a homogeneous, red-brown, very easily flowable liquid with an active iodine content of 0.5 weight percent which when diluted to a disinfectant cleansing solution containing 20 ppm of active iodine had a surface tension of 31.5 dyne/cm and is particularly suited for automatic bottle purification disinfection.

EXAMPLE 4

There were introduced into an open container equipped with a mechanical dispenser at room temperature and in the following sequence in succession
6 parts of glacial acetic acid
30 parts of water
4 parts of Iodophor B and in portions
10 parts of 85% phosphoric acid
and the mixture stirred about 30 minutes.

Then there were stirred in within 1 hour via a dosaging shaking trough 50 parts of china clay having an average particle size of 1 micron.

The dispersion formed having an active iodine content of 0.6 weight percent was homogeneous and had a viscosity of 700 cps. This dispersion contains as the outer, continuous phase an iodophor solution with an active iodine content of 1.2 weight percent which can be recovered in about 60% yield from the dispersion by pressure membrane filtration.

The iodine containing dispersion is particularly suited as a disinfecting cleansing agent for treatment of skin diseases in veterinary medicine.

EXAMPLE 5

There were introduced into an open container equipped with a mechanical stirrer at room temperature and in the following sequence in succession
20 parts of glacial acetic acid
5 parts of sodium dodecyl benzene sulfonate, as an 80% paste
36.7 parts of water
13.3 parts of Iodophor B and in portions
25 parts of 85% phosphoric acid
and the mixture stirred about 30 minutes.

The iodophor solution formed thereby is a homogeneous, deep red-brown liquid with 2 weight percent of active iodine which when diluted to a disinfectant cleansing solution containing 50 ppm of active iodine had a surface tension of 33 dyne/cm, only foamed weakly and is particularly suited as a purification disinfection agent for milk cans and milk containers of dairies.

EXAMPLE 6

Into a closed heatable and coolable container equipped with a mechanical kneader and a motor driven discharge screw below the bottom valve there were introduced at 40° C internal temperature and in the following sequence in succession
12 parts of glacial acetic acid
2 parts of high molecular weight polyacrylic acid with an average molecular weight of above
1 million (Carbopol 940 manufactured by B. F. Goodrich)
22.7 parts of water
10 parts of sodium dihexyl sulfosuccinate 50% (balance water and isopropanol)
13.3 parts of Iodophor B and in portions
10 parts of 85% phosphoric acid
and the mixture stirred for 5 to 10 minutes.

After the cooling of the reaction mass to room temperature within 1 hour there were stirred in by means of a dosaging conveyor type weigher 30 parts of pumice sieved or air classified to a particle size below 10 microns. The dispersion formed was homogeneous and had a viscosity of about 40,000 cps. It had an active iodine content of 2 weight percent and is particularly suited as a disinfecting washing paste.

The homogeneous continuous phase of this dispersion consists of an iodophor solution of the invention containing 2.85 weight percent of active iodine which can be recovered by pressure membrane filtration in a yield of 55%.

EXAMPLE 7

There were introduced into an open container equipped with a mechanical stirrer at room temperature and in the following sequence in succession
30 parts of glacial acetic acid
30 parts of water
10 parts of Iodophor C and in portions
30 parts of 85% phosphoric acid
and the mixture stirred for about 30 minutes.

The iodophor solution formed thereby is a homogeneous, deep red-brown easily flowable liquid with an active iodine content of 2 weight percent which as such and also when diluted to a disinfectant solution containing 25 ppm of active iodine did not form any foam and therefore is particularly suited for disinfection in high pressure spraying processes using relatively very hard dilution water up to 40° dH.

EXAMPLE 8

There were introduced into an open container equipped with a mechanical stirrer at room temperature and in the following sequence in succession
20 parts of glacial acetic acid
5 parts of sodium dihexyl sulfosuccinate as a 75% solution in a propanol-water mixture
35 parts of water
10 parts of Iodophor C and in portions
30 parts of 85% phosphoric acid and the mixture stirred about 30 minutes.

The iodophor solution formed thereby is a homogeneous, deep red-brown, easily flowable liquid with an active iodine content of 2% which as such only foams weakly and when diluted to a disinfectant cleansing solution having a surface tension of 39.5 dyne/cm did not foam. Therefore, it is particularly suited as a disinfectant cleansing agent for spray cleaning or disinfection in pharmaceutical or brewery operations.

EXAMPLE 9

There were introduced into a closed heatable and coolable stirred container at 35° C internal temperature and in the following sequence in succession
- 15 parts of glacial acetic acid
- 2 parts of sodium lauryl sulfate as a 96% powder
- 1 part of sodium dihexyl sulfosuccinate as a 75% solution in a propanol-water-mixture
- 52 parts of a propanol-water-mixture
- 15 parts of Iodophor C and in portions
- 15 parts of 85% phosphoric acid and the mixture stirred about 5 minutes.

The iodophor solution formed thereby is a homogeneous, easily flowable, deep dark red-brown solution with an active iodine content of 3 weight percent which when diluted to a disinfectant cleansing solution containing 50 ppm of active iodine and having a surface tension of 32.5 dyne/cm only foamed weakly and is particularly suited for spray purification or disinfection of animal stalls, cages or laying batteries.

EXAMPLE 10

There were introduced into a closed heatable and coolable stirred container with an ascending condenser and suitable feeding or dosaging devices at room temperature
- 25 parts of water
- 30 parts of glacial acetic acid
- 20 parts of an acrolein-acrylic acid copolymer having an average molecular weight of 2000 and an acid equivalent weight of 100 produced by oxidative copolymerization of 30 parts by weight of acrylic acid and 70 parts by weight of acrolein
- 3 parts of crude iodine 98% and
- 2 parts of sodium dihexyl sulfosuccinate as a 75% solution in a propanol-water-mixture and the mixture stirred for 3 to 4 hours at an internal temperature of 60° to 70° C.

After the cooling to room temperature there were added in portions 20 parts of 85% phosphoric acid. After about 30 minutes of stirring the mixture was filtered over a porcelain frit (pore size G4) whereby as a rule no residue remained on the porcelain frit.

The iodophor solution formed is a homogeneous, readily flowable, deep red-brown liquid with an active iodine content of about 3 weight percent active iodine which as such only foamed slightly and when diluted to a disinfectant solution containing 20 ppm of active iodine with a surface tension of 45.2 dyne/cm did not foam. It is particularly suited for a disinfectant solution for high pressure spray disinfectant cleansing when using average hardness dilution water up to about 20° dH.

What is claimed is:

1. An aqueous iodophor solution comprising water and
   (a) 0.5 to 3 weight percent iodine
   (b) 10 to 30 weight percent phosphoric acid
   (c) 5 to 30 weight percent acetic acid, and
   (d) 0.5 to 20 weight percent of a polymer having an average molecular weight between 500 and 10,000 and consisting essentially of repeating units of the general formula

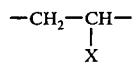

where X in 90 to 65% of the cases in COOH, in 10 to 35% of the cases in

and in 0 to 10% of the cases is selected from the group consisting of (1) CH$_2$OH, (2) CN, (3)

and (4) mixtures of at least two of (1), (2) and (3), the X side chain groups being distributed statistically at random.

2. An iodophor solution according to claim 1 consisting essentially of (a), (b), (c), (d) and water.

3. An aqueous iodophor solution according to claim 1 also including either (I) 0.1 to 10 weight percent of a monohydric alkanol having 1 to 4 carbon atoms, (II) 0.1 to 3 weight percent of an iodide selected from the group consisting of hydrogen iodide, alkali metal iodide, alkaline earth metal iodide and ammonium iodide, (III) 0.5 to 5 weight percent of an anionic detergent or (IV) a mixture of at least two of (I), (II) and (III).

4. An iodophor solution according to claim 3 consisting essentially of the stated materials.

5. An iodophor solution according to claim 4 wherein (III) is sodium dihexyl sulfosuccinate, sodium lauryl sulfate, sodium dodecyl benzene sulfonate or mixtures thereof.

6. An iodophor solution according to claim 3 including (I).

7. An iodophor solution according to claim 3 including (II).

8. An iodophor solution according to claim 3 including (III).

9. An aqueous solution obtained by diluting the iodophor solution according to claim 8 with sufficient water to have a surface tension between 30 and 45.2 dyne/cm.

10. A diluted solution according to claim 9 wherein (III) is dihexyl sulfosuccinate, sodium lauryl sulfate, sodium dodecyl benzene sulfonate or a mixture thereof.

11. An iodophor solution according to claim 3 consisting of (a), (b), (c), (d), water and at least one of (I) and (II).

12. An iodophor solution according to claim 11 containing (I) but not (II).

13. An iodophor solution according to claim 11 containing (II) but not (I).

14. An iodophor solution according to claim 1 wherein all of the X units are COOH or

15. An iodophor solution according to claim 14 consisting of (a), (b), (c), (d) and water.

16. An iodophor solution according to claim 14 consisting of (a), (b), (c), (d), water and at least one of (I) 0.1 to 10 weight percent of a monohydric alkanol having 1 to 4 carbon atoms, (II) 0.1 to 3 weight percent of an iodide selected from the group consisting of hydrogen iodide, alkali metal iodide, alkaline earth metal iodide and ammonium iodide, (III) 0.5 to 5 weight percent of an anionic detergent and (IV) a mixture of at least two of (I), (II) and (III).

17. An iodophor solution according to claim 16 free of anionic detergent.

18. An iodophor solution according to claim 16 containing anionic detergent.

19. An aqueous iodophor solution according to claim 1 consisting essentially of water in an amount to make up to 100 weight percent together with either (A) (a), (b), (c) and (d) or (B) (a), (b), (c), (d) and also including either (I) 0.1 to 10 weight percent of a monohydric alkanol having 1 to 4 carbon atoms, (II) 0.1 to 3 weight percent of an iodide selected from the group consisting of hydrogen iodide, alkali metal iodide, alkaline earth metal iodide and ammonium iodide, (III) 0.5 to 5 weight percent of an anionic detergent or (IV) a mixture of at least two of (I), (II) and (III).

* * * * *